(12) United States Patent
Schönrock et al.

(10) Patent No.: US 6,399,046 B1
(45) Date of Patent: Jun. 4, 2002

(54) USE OF A CONTENT OF CATECHINS OR A CONTENT OF GREEN TEA EXTRACT IN COSMETIC PREPARATIONS FOR TANNING THE SKIN

(75) Inventors: Uwe Schönrock, Nahe; Heiner Max, Hamburg, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/719,667

(22) PCT Filed: Jun. 16, 1999

(86) PCT No.: PCT/EP99/04146

§ 371 (c)(1),
(2), (4) Date: Mar. 5, 2001

(87) PCT Pub. No.: WO99/66897

PCT Pub. Date: Dec. 29, 1999

(30) Foreign Application Priority Data

Jun. 20, 1998 (DE) .......................................... 198 27 624

(51) Int. Cl.[7] .............................. A61K 7/42; A61K 7/44; A61K 7/00
(52) U.S. Cl. ............................. 424/59; 424/60; 424/401
(58) Field of Search .............................. 424/59, 60, 401

(56) References Cited

U.S. PATENT DOCUMENTS

| | | | | |
|---|---|---|---|---|
| 4,515,773 A | * | 5/1985 | Herlihy | 424/59 |
| 4,708,865 A | * | 11/1987 | Turner | 424/59 |
| 4,981,485 A | * | 1/1991 | Motono | 8/405 |
| 5,705,145 A | * | 1/1998 | Miklean et al. | 424/59 |

FOREIGN PATENT DOCUMENTS

| | | | |
|---|---|---|---|
| DE | 19704384 C1 | * | 4/1998 |
| JP | 09194493 A | * | 7/1997 |

* cited by examiner

*Primary Examiner*—Jose' G. Dees
*Assistant Examiner*—Marina Lamm
(74) *Attorney, Agent, or Firm*—Norris, McLaughlin & Marcus

(57) ABSTRACT

The use of catechins or gallic esters of catechins or aqueous or organic extracts from plants or parts of plants which have a content of catechins or gallic esters of catechins, for example the leaves of the plant family Theaceae, in particular of the species *Camellia sinensis* (green tea) or a typical ingredient thereof (such as, e.g. polyphenols or catechins, caffeine, vitamins, sugars, minerals, amino acids, lipids), for intensifying natural skin tanning or for stimulating melanogenesis in human skin.

7 Claims, No Drawings

USE OF A CONTENT OF CATECHINS OR A CONTENT OF GREEN TEA EXTRACT IN COSMETIC PREPARATIONS FOR TANNING THE SKIN

This application is a 371 of PCT/EP99/04146, which was filed on Jun. 16, 1999.

The present invention relates to cosmetic and dermatological preparations for tanning the skin, in particular to those which also offer protection against UV radiation.

The harmful effect of the ultraviolet part of solar radiation on the skin is generally known. While rays having a wavelength of less than 290 nm (the UVC region), are absorbed by the ozone layer in the earth's atmosphere, rays in the range between 290 nm and 320 nm, the UVB region, cause erythema, simple sunburn or even burns of varying severity.

The erythema activity maximum of sunlight is given as the relatively narrow region around 308 nm.

Numerous compounds are known for protecting against UVB radiation; these are mostly derivatives of 3-benzylidenecamphor, of 4-aminobenzoic acid, of cinnamic acid, of salicylic acid, of benzophenone and also of 2-phenylbenzimidazole.

It is also important to have available filter substances for the range between about 320 nm and about 400 nm, the UVA region, since its rays can also cause damage. Thus, it has been found that UVA radiation leads to damage of the elastic and collagenous fibers of connective tissue, causing premature aging of the skin, and that it is to be regarded as a cause of numerous phototoxic and photoallergic reactions. The harmful effect of UVB radiation can be intensified by UVA radiation. In addition, UVA radiation can cause skin damage by damaging keratin or elastin in the skin. This leads to a reduction in elasticity and water-storage capacity, i.e. the skin becomes less supple and tends towards wrinkling. The notably high incidence of skin cancer in regions where solar irradiation is strong indicates that damage to the genetic information in cells is also apparently caused by sunlight, specifically by UVA radiation.

However, UV radiation can also lead to photochemical reactions, the photochemical reaction products interfering with the skin's metabolism.

Such photochemical reaction products are predominantly free-radical compounds, e.g. hydroxyl radicals. Undefined free-radical photoproducts which are formed in the skin itself can also display uncontrolled secondary reactions as a result of their high reactivity. However, singlet oxygen, a non-free-radical excited state of the oxygen molecule, can also arise during UV irradiation, as can short-lived epoxides and many others. Singlet oxygen, for example, differs from the normal triplet oxygen (free-radical ground state) by virtue of its increased reactivity. However, excited, reactive (free-radical) triplet states of the oxygen molecule also exist.

UV radiation is also a type of ionizing radiation. There is therefore the risk that ionic species may also arise during UV exposure, which then, for their part, are capable of oxidative intervention in the biochemical processes.

The pigmentation of human skin is essentially brought about by the presence of melanin. Melanin and its degradation products (melanoids), carotene, degree of perfusion, and the condition and thickness of the Stratum corneum and other skin layers permit skin shades from virtually white (in cases of reduced filling or in cases of an absence of blood vessels) or yellowish via pale brown-reddish, bluish to brown of different shades and finally almost black. The individual regions of the skin display differing depths of shade as a result of varying amounts of melanin.

Natural melanin protects the skin from penetrating UV radiation. The number of melanin granules produced in the melanocytes determines whether a person has pale skin or dark skin. In cases of strong pigmentation (e.g. in colored races, but also in those with pale skin following UV irradiation) melanin is also to be found in the Stratum spinosum and even in the Stratum corneum. It attenuates the UV radiation by up to about 90% before it reaches the corium.

Depending on their sensitivity to light, the skin types below are normally differentiated:

Skin type I never tans, always burns.

Skin type II rarely tans, burns easily.

Skin type III tans averagely well.

Skin type IV tans easily to give a lasting tan, almost never burns.

Skin type V dark, often almost black skin, never burns.

The natural shielding from harmful UV radiation is a tangible advantage of natural skin tanning. Moreover, for many decades a "healthy" skin color has been a sign of, in particular, sporting activity and is therefore considered to be desirable by a broad section of consumers. Representatives of skin types I and II who wish to enjoy such a skin shade in any case therefore have to rely on self-tanning preparations. However, representatives of skin type IIII who do not wish to excessively be exposed to the risks of sunbathing but nevertheless want to appear tanned are also thankful target groups for self-tanning preparations.

Artificial skin tanning can be brought about in a cosmetic or medicinal way, the following approaches essentially playing a role:

The regular taking of carotene preparations results in carotene being stored in the subcutaneous fatty tissue, and the skin gradually turns orange to yellow-brown.

Using make-up preparations which can be washed off it is possible to achieve a slight skin shading (e.g. extracts of fresh green walnut shells, henna).

Coloring can also take place via the route of a chemical change in the horny layer of the skin using self-tanning preparations. The most important active ingredient is dihydroxyacetone (DHA). The skin tanning achieved in this way cannot be washed off and is removed only with the normal flaking of the skin (after about 10–15 days). Dihydroxyacetone can be referred to as ketotriose and reacts as a reducing sugar with the amino acids of the skin and the free amino and imino groups of keratin via a number of intermediates in the sense of a Maillard reaction to give brown-colored substances, so-called melanoids, which are sometimes also called melanoidins.

A disadvantage of tanning with dihydroxyacetone is that the skin tanned therewith is not protected from sunburn, in contrast to "sun-tanned" skin.

A further disadvantage of dihydroxyacetone is that, particularly under the influence of ultraviolet radiation, formaldehyde is eliminated, albeit in small amounts in most cases. There was therefore an urgent need to find ways in which the decomposition of dihydroxyacetone can be effectively countered.

To overcome the disadvantages of the prior art was therefore the object of the present invention.

It was therefore surprising and could not have been foreseen by the person skilled in the art that the use of catechins or gallic esters of catechins or aqueous or organic extracts from plants or parts of plants which have a content of catechins or gallic esters of catechins, for example the leaves of the Theaceae plant family, in particular of the species Camellia sinensis (green tea) or typical ingredients thereof (such as e.g. polyphenols or catechins, caffeine, vitamins, sugars, minerals, amino acids, lipids) for intensifying natural skin tanning or for stimulating melanogenesis in human skin would overcome the disadvantages of the prior art.

Catechins are a group of compounds which are to be regarded as hydrated flavones or anthocyanidines. The catechins form the base substance of a series of natural oligo- or polymeric tannins, e.g. in tea. They occur together with other phenols in many types of fruit and are involved in the browning, catalyzed by phenol oxidases, of areas which have been subjected to pressure or have been cut (e.g. in the case of apples).

The base substance "catechin" (catechol, 3,3',4',5,7-flavanpentol, 2-(3,4-dihydroxy-phenyl)chroman-3,5,7-triol) is widespread in plants and occurs, for example, in the catechu. It is characterized by the structural formula

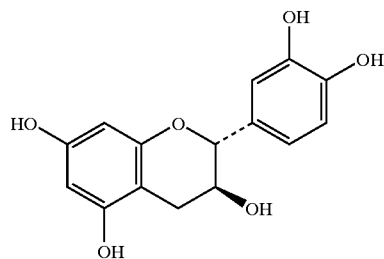

Epicatechin ((2R,3R)-3,3',4',5,7-flavanpentol) is an epimer of catechin and is characterized by the structural formula

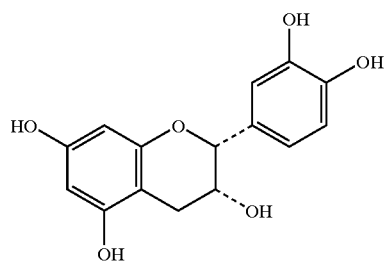

The objects according to the invention are likewise achieved by cosmetic or dermatological preparations comprising vegetable extracts having a content of catechins, in particular those preparations which comprise green tea extracts.

Tea originates exclusively from leaves, leaf buds and delicate stems of the tea plant (*Camellia sinensis* L.), which are processed by methods such as withering, rolling, fermentation, comminution and drying. Black tea is a fermented tea, oolong tea is a semifermented tea whose leaves, following withering and rolling, are fermented for only half of the otherwise customary period and then dried. Green tea is an unfermented product whose leaves are blanched, rolled and dried with retention of the natural leaf dyes.

The composition of the ingredients of tea leaves varies considerably depending on the origin and treatment. On average, black tea comprises 18.9% catechins and catechin tannins, 16.6% proteins, 2.7% caffeine, 10.2% other nitrogen compounds, 4.6% oligosaccharides, 0.6% starch, 11.9% pectin, 7.9% cellulose and 6.1% lignin.

Fresh leaves have essentially the same composition but comprise more catechins (26%), fewer nitrogen compounds (8.7%, at the same caffeine content), and 0.8% inositol. The polyphenol tannins comprise about 80% catechins (main constituent galloyl-(−)-epigallocatechin).

Surprisingly, it has been found that extracts from leaves of plants of the Theales order with the Theaceae family, in particular the species Camellia spec., very particularly the tea types *Camellia sinenis, C. assamica, C. taliensis* and *C. irrawadiensis* and hybrids of these with, for example, *Camellia japonica* increase the activity of melanocytes in human skin and intensify natural skin tanning.

Apart from the catechins (for example catechin and epicatechin), green tea also comprises the gallic esters of these active ingredients, which are likewise effective according to the invention.

Skincare products according to the invention advantageously comprise 0.0001–20 percent by weight of catechins or gallic esters of catechins or of aqueous or organic extracts from plants or parts of plants which have a content of catechins or gallic esters of catechins, preferably polyphenols or catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin and (−)-epigallocatechin gallate.

Cosmetic or dermatological preparations according to the invention preferably comprise 0.001–10% by weight of catechins or gallic esters of catechins or of aqueous or organic extracts from plants or parts of plants which have a content of catechins or gallic esters of catechins, based on the total composition of the preparations.

Cosmetic or dermatological preparations according to the invention very particularly preferably comprise 0.01–1% by weight of catechins or gallic esters of catechins or of aqueous or organic extracts from plants or parts of plants which have a content of catechins or gallic esters of catechins, based on the total composition of the preparations.

According to the invention the cosmetic and/or dermatological light protection formulations can have the customary composition and be used for cosmetic and/or dermatological light protection, and also for the treatment, care and cleansing of skin and/or hair and as a make-up product in decorative cosmetics.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously, these can additionally comprise at least one further UVA filter and/or at least one further UVB filter and/or at least one inorganic pigment, preferably an inorganic micropigment.

According to the invention the cosmetic and dermatological preparations can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favourable antioxidants which can be used are any antioxidants suitable or customary for cosmetic and/or dermatological applications.

It is also advantageous to add antioxidants to the preparations according to the invention. The antioxidants are advantageously selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximines) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active substances which are suitable according to the invention.

The amount of the abovementioned antioxidants (one or more compounds) in the preparations is preferably from 0.001 to 30% by weight, particularly preferably from 0.05 to 20% by weight, especially 1–10% by weight, based on the total weight of the preparation.

If vitamin E and/or derivatives thereof are used as the antioxidant or antioxidants, their respective concentrations are advantageously chosen from the range of 0.001–10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

The lipid phase can advantageously be chosen from the following group of substances:
mineral oils, mineral waxes
oils, such as triglycerides of capric or caprylic acid, but preferably castor oil;
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alkyl benzoates;
silicone oils such as dimethylpolysiloxanes, diethylpolysiloxanes, diphenyl-polysiloxanes and mixtures thereof.

For the purposes of the present invention, the oil phase of the emulsions, oleogels and hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Such ester oils can advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oil phase can also advantageously be chosen from the group of branched and unbranched hydrocarbons and hydrocarbon waxes, silicone oils, dialkyl ethers, from the group of saturated or unsaturated, branched or unbranched alcohols, and also fatty acid triglycerides, namely the triglycerol esters of saturated and/or unsaturated, branched and/or unbranched alkanecarboxylic acids of chain length from 8 to 24, in particular 12–18, carbon atoms. The fatty acid triglycerides can advantageously be chosen, for example, from the group of synthetic, semisynthetic and natural oils, e.g. olive oil, sunflower oil, soybean oil, peanut oil, rapeseed oil, almond oil, palm oil, coconut oil, palm kernel oil and the like.

For the purposes of the present invention, any mixtures of such oil and wax components can also advantageously be used. When required, it can also be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, ipsoeicosane, 2-ethylhexyl cocoate, $C_{12-15}$-alkyl benzoate, caprylic/capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethyl-hexyl isostearate and isotridecyl isononanoate are particularly advantageous.

Of the hydrocarbons, paraffin oil, squalane and squalene are advantageously to be used for the purposes of the present invention.

The oil phase can advantageously also contain cyclic or linear silicone oils or can consist entirely of such oils, although it is preferable to use an additional content of other oil phase components in addition to the silicone oil or silicone oils.

Cyclomethicone (octamethylcyclotetrasiloxane) is advantageously used as the silicone oil to be used according to the invention. However, other silicone oils can advantageously be used for the purpose of the present invention, for example hexamethylcyclotrisiloxane, polydimethylsiloxane, poly (methylphenylsiloxane).

Mixtures of cyclomethicone and isotridecyl isononanoate and mixtures of cyclomethicone and 2-ethylhexyl isostearate are particularly advantageous.

The aqueous phase of the preparations according to the invention may advantageously comprise alcohols, diols or polyols of low carbon number, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and especially one or more thickeners which can advantageously be selected from the group consisting of silicon dioxide, aluminum silicates and polysaccharides and derivatives thereof, e.g. hyaluronic acid, xanthan gum, hydroxypropylmethylcellulose, and particularly advantageously from the group of polyacrylates, preferably a polyacrylate from the group consisting of the so-called Carbopols, for example Carbopol grades 980, 981, 1382, 2984, 5984, in each case individually or in combination.

The preparations according to the invention can advantageously also comprise substances which absorb UV radiation in the UVB region, the total amount of the filter substances being, for example, 0.1% by weight to 30% by weight, preferably 0.5 to 10% by weight, in particular 1.0 to 6.0% by weight, based on the total weight of the preparations, in order to provide cosmetic preparations which protect the hair and/or skin from the entire region of ultraviolet radiation. They can also serve as sunscreens for the hair.

If the preparations according to the invention comprise UVB filter substances, these may be oil-soluble or water-soluble. Examples of oil-soluble UVB filters which are advantageous according to the invention are:

3-benzylidenecamphor derivatives, preferably 3-(4-methylbenzylidene)-camphor, 3-benzylidenecamphor;

4-aminobenzoic acid derivatives, preferably 2-ethylhexyl 4-(dimethylamino)-benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxy-benzalmalonate, 2,4,6-trianilino(p-carbo-2'-ethyl-1'-hexyloxy)-1,3,5-triazine.

Advantageous water-soluble UVB filters are e.g.:

salts of 2-phenylbenzimidazol-5-sulfonic acid, such as its sodium, potassium or its triethanolammonium salt, and the sulfonic acid itself;

sulfonic acid derivatives of benzophenones, preferably 2-hydroxy-4-methoxybenzophenone-5-sulfonic acid and its salts;

sulfonic acid derivatives of 3-benzylidenecamphor, such as e.g. 4-(2-oxo-3-bornylidenemethyl)benzenesulfonic acid, 2-methyl-5-(2-oxo-3-bornylidene-methyl)sulfonic acid and its salts, and 1,4-di(2-oxo-10-sulfo-3-bornylidene-methyl)benzene and salts thereof (the corresponding 10-sulfato compounds, for example the corresponding sodium, potassium or triethanolammonium salt), also referred to as benzene-1,4-di(2-oxo-3-bornylidenemethyl-10-sulfonic acid.

The list of said UVB filters which can be used in combination with the active ingredient combinations according to the invention is not of course intended to be limiting.

It may also be advantageous to use UVA filters which are customarily present in cosmetic preparations. These substances are preferably derivatives of dibenzoylmethane, in particular 1-(4'-tert-butylphenyl)-3-(4'-methoxyphenyl) propane-1,3-dione and 1-phenyl-3-(4'-isopropylphenyl) propane-1,3-dione. The amounts which can be used are those used for the UVB combination.

The total amount of dibenzoylmethanes, in particular 4-(tert-butyl)-4'-methoxy-dibenzoylmethane in the finished cosmetic or dermatological preparations is advantageously chosen from the range 0.1–10.0% by weight, preferably 0.5–6.0% by weight, based on the total weight of the preparations.

The total amount of camphor derivatives, in particular 4-methylbenzylidenecamphor and/or benzylidenecamphor, in the finished cosmetic or dermatological preparations is advantageously chosen from the range 0.1–10.0% by weight, preferably 0.5–6.0% by weight, based on the total weight of the preparations.

The total amount of triazine derivatives, in particular tris(2-ethylhexyl) 4,4',4"-(1,3,5-triazine-2,4,6-triyltriimino) trisbenzoate, in the finished cosmetic or dermatological preparations is advantageously chosen from the range 0.1–10.0% by weight, preferably 0.5–6.0% by weight, based on the total weight of the preparations.

Cosmetic and dermatological preparations according to the invention also advantageously comprise, although it is not obligatory, inorganic pigments based on metal oxides and/or other metal compounds which are insoluble or virtually insoluble in water, in particular the oxides of titanium ($TiO_2$), Zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides. Particular preference is given to pigments based on $TiO_2$.

According to the invention, the inorganic pigments are in hydrophobic form, i.e. they have been surface-treated to repel water. This surface treatment may involve providing the pigments with a thin hydrophobic layer by methods known per se.

One such method involves, for example, producing the hydrophobic surface layer by a reaction in accordance with

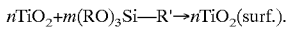

Here, n and m are stoichiometric parameters to be used as desired, and R and R' are the desired organic radicals. For example, hydrophobicized pigments prepared analogously to DE-A 33 14 742 are advantageous.

Advantageous $TiO_2$ pigments are available, for example, under the trade name T 805 from Degussa.

The total amount of inorganic pigments, in particular hydrophobic inorganic pigments, in the finished cosmetic or dermatological preparations is advantageously chosen from the range 0.1–30% by weight, preferably 0.1–10.0, in particular 0.5–6.0% by weight, based on the total weight of the preparations.

In addition, according to the invention it may optionally be advantageous to provide the preparations with further UVA and/or UVB filters, for example certain salicylic acid derivatives such as

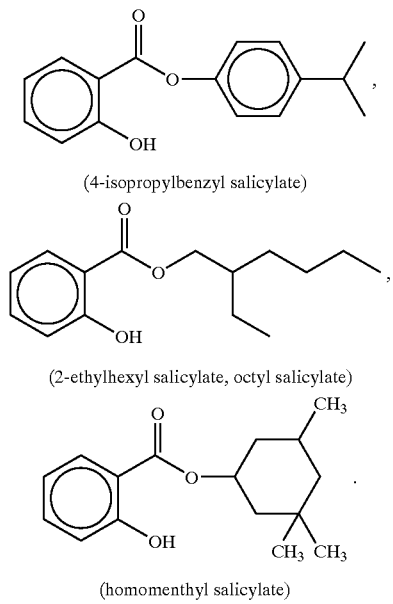

(4-isopropylbenzyl salicylate)

(2-ethylhexyl salicylate, octyl salicylate)

(homomenthyl salicylate)

The total amount of one or more salicylic acid derivatives in the finished cosmetic or dermatological preparations is advantageously chosen from the range 0.1–15.0% by weight, preferably 0.5–8.0% by weight, based on the total weight of the preparations. If ethylhexyl salicylate is chosen, it is advantageous to choose the total amount thereof from the range 0.1–5.0% by weight, preferably 0.5–2.5% by weight. If homomenthyl salicylate is chosen, it is advantageous to choose the total amount thereof from the range 0.1–10.0% by weight, preferably 0.5–5.0% by weight.

A further additional light protection filter substance which is to be used advantageously in accordance with the invention is ethylhexyl 2-cyano-3,3-diphenyl acrylate (octocrylene), which is available from BASF under the name UVINUL® N 539 and is characterized by the following structure:

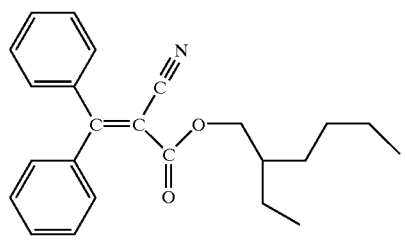

The examples below serve to illustrate the present invention without limiting it. Unless stated otherwise, all amounts, proportions and percentages are based on the weight and the total amount or on the total weight of the preparations.

EXAMPLE 1

| W/O cream | % by weight |
|---|---|
| Paraffin oil (German Pharmacopoeia (GP) 9) | 10.00 |
| Petrolatum | 4.00 |

| W/O cream | % by weight |
|---|---|
| Wool wax alcohol | 1.00 |
| PEG-7 hydrogenated castor oil | 3.00 |
| Aluminum stearate | 0.40 |
| α-Glucosylrutin | 0.50 |
| Glycerol | 2.00 |
| Preservatives, dyes, perfume | q.s. |
| Epigallocatechin gallate | 0.20 |
| Water | ad 100.00 |

EXAMPLE 2

| W/O Lotion | % by weight |
|---|---|
| Paraffin oil (GP 9) | 20.00 |
| Petrolatum | 4.00 |
| Glucose sesquiisostearate | 2.00 |
| Aluminum stearate | 0.40 |
| α-Glucosylrutin | 0.30 |
| α-Tocopheryl acetate | 1.00 |
| Glycerol | 5.00 |
| Preservatives, dyes, perfume | q.s. |
| Epigallocatechin gallate | 0.50 |
| Water | ad 100.00 |

EXAMPLE 3

| O/W lotion | % by weight |
|---|---|
| Paraffin oil (GP 9) | 8.00 |
| Isopropyl palmitate | 3.00 |
| Petrolatum | 4.00 |
| Cetylstearyl alcohol | 2.00 |
| PEG 40 castor oil | 0.50 |
| Sodium cetylstearyl sulfate | 0.50 |
| Sodium carbomer | 0.40 |
| α-Glucosylrutin | 0.50 |
| Glycerol | 3.00 |
| α-Tocopherol | 0.20 |
| Octyl methoxycinnamate | 5.00 |
| Butylmethoxydibenzoylmethane | 1.00 |
| Preservatives, dyes, perfume | q.s. |
| Epigallocatechin gallate | 0.05 |
| Water | ad 100.00 |

EXAMPLE 4

| O/W cream | % by weight |
|---|---|
| Paraffin oil (GP 9) | 7.00 |
| Avocado oil | 4.00 |
| Glyceryl monostearate | 2.00 |
| α-Glucosylrutin | 0.80 |
| α-Tocopheryl acetate | 1.50 |
| Sodium lactate | 3.00 |

-continued

O/W cream

| | % by weight |
|---|---|
| Glycerol | 3.00 |
| Preservatives, dyes, perfume | q.s. |
| Epigallocatechin gallate | 3.00 |
| Water | ad 100.00 |

EXAMPLE 5

Liposome-containing gel

| | % by weight |
|---|---|
| Lecithin | 6.00 |
| Shea butter | 3.00 |
| α-Glucosylrutin | 0.50 |
| α-Tocopherol | 0.20 |
| Mg ascorbyl phosphate | 0.80 |
| Sodium citrate | 0.50 |
| Glycine | 0.20 |
| Urea | 0.20 |
| Sodium PCA | 0.50 |
| Hydrolyzed collagen | 2.00 |
| Xanthan gum | 1.40 |
| Sorbitol | 3.00 |
| Preservatives, dyes, perfume | q.s. |
| Epigallocatechin gallate | 1.20 |
| Water | ad 100.00 |

EXAMPLE 6

Sunscreen emulsion

| | % by weight |
|---|---|
| Cyclomethicone | 2.00 |
| Cetyldimethicone copolyol | 0.20 |
| PEG 22 dodecyl copolymer | 3.00 |
| Paraffin oil (GP 9) | 2.00 |
| Caprylic/capric triglyceride | 5.80 |
| Octyl methoxycinnamate | 5.80 |
| Butylmethoxydibenzoylmethane | 4.00 |
| α-Glucosylrutin | 0.25 |
| Epigallocatechin gallate | 0.50 |
| α-Tocopheryl acetate | 0.50 |
| ZnSO$_4$ | 0.70 |
| Na$_4$EDTA | 0.30 |
| Preservatives, dyes, perfume | q.s. |
| Water | ad 100.00 |

EXAMPLE 7

Sunscreen emulsion

| | % by weight |
|---|---|
| Cyclomethicone | 2.00 |
| Cetylstearyl alcohol + PEG 40 hydrogenated castor oil + sodium cetylstearyl sulfate | 2.50 |
| Glyceryl lanolate | 1.00 |
| Caprylic/capric triglyceride | 0.10 |
| Laurylmethicone copolyol | 2.00 |
| Octyl stearate | 3.00 |

-continued

Sunscreen emulsion

| | % by weight |
|---|---|
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.50 |
| α-Glucosylrutin | 0.10 |
| Epigallocatechin gallate | 0.20 |
| α-Tocopheryl acetate | 1.00 |
| Na$_3$HEDTA | 1.50 |
| Preservatives, dyes, perfume | q.s. |
| Mg ascorbyl phosphate | 0.50 |
| Water | ad 100.00 |

EXAMPLE 8

Sunscreen emulsion

| | % by weight |
|---|---|
| Cyclomethicone | 2.00 |
| Cetylstearyl alcohol + PEG 40 hydrogenated castor oil + sodium cetylstearyl sulfate | 2.50 |
| Glyceryl lanolate | 1.00 |
| Caprylic/capric triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octylmethoxy cinnamate | 5.00 |
| Butylmethoxydibenzoylmethane | 0.75 |
| α-Glucosylrutin | 0.50 |
| Na$_3$HEDTA | 1.50 |
| Preservatives, dyes, perfume | q.s. |
| Epigallocatechin gallate | 3.00 |
| Water | ad 100.00 |

EXAMPLE 9

Spray formulation

| | % by weight |
|---|---|
| Epigallocatechin gallate | 0.30 |
| Dihydrorobinetin | 0.80 |
| Ethanol | 28.20 |
| Preservatives, dyes, perfume | q.s. |
| Propane/butane 25/75 | ad 100.00 |

EXAMPLE 10

W/O cream

| | % by weight |
|---|---|
| Paraffin oil (GP 9) | 10.00 |
| Petrolatum | 4.00 |
| Wool wax alcohol | 1.00 |
| PEG-7 hydrogenated castor oil | 3.00 |

-continued

W/O cream

| | % by weight |
|---|---|
| Aluminum stearate | 0.40 |
| α-Glucosylrutin | 0.50 |
| Glycerol | 2.00 |
| Preservatives, dyes, perfume | q.s. |
| Green tea extract | 0.20 |
| Water | ad 100.00 |

EXAMPLE 11

W/O lotion

| | % by weight |
|---|---|
| Paraffin oil (GP 9) | 20.00 |
| Petrolatum | 4.00 |
| Glucose sesquiisostearate | 2.00 |
| Aluminum stearate | 0.40 |
| α-Glucosylrutin | 0.30 |
| α-Tocopheryl acetate | 1.00 |
| Glycerol | 5.00 |
| Preservatives, dyes, perfume | q.s. |
| Green tea extract | 0.50 |
| Water | ad 100.00 |

EXAMPLE 12

O/W lotion

| | % by weight |
|---|---|
| Paraffin oil (GP 9) | 8.00 |
| Isopropyl palmitate | 3.00 |
| Petrolatum | 4.00 |
| Cetylstearyl alcohol | 2.00 |
| PEG 40 castor oil | 0.50 |
| Sodium cetylstearyl sulfate | 0.50 |
| Sodium carbomer | 0.40 |
| α-Glucosylrutin | 0.50 |
| Glycerol | 3.00 |
| α-Tocopherol | 0.20 |
| Octyl methoxycinnamate | 5.00 |
| Butylmethoxydibenzoylmethane | 1.00 |
| Preservatives, dyes, perfume | q.s. |
| Green tea extract | 0.05 |
| Water | ad 100.00 |

EXAMPLE 13

O/W cream

| | % by weight |
|---|---|
| Paraffin oil (GP 9) | 7.00 |
| Avocado oil | 4.00 |
| Glyceryl monostearate | 2.00 |
| α-Glucosylrutin | 0.80 |
| α-Tocopheryl acetate | 1.50 |
| Sodium lactate | 3.00 |
| Glycerol | 3.00 |
| Preservatives, dyes, perfume | q.s. |

-continued

O/W cream

| | % by weight |
|---|---|
| Green tea extract | 3.00 |
| Water | ad 100.00 |

EXAMPLE 14

Liposome-containing gel

| | % by weight |
|---|---|
| Lecithin | 6.00 |
| Shea butter | 3.00 |
| α-Glucosylrutin | 0.50 |
| α-Tocopherol | 0.20 |
| Mg ascorbyl phosphate | 0.80 |
| Sodium citrate | 0.50 |
| Glycine | 0.20 |
| Urea | 0.20 |
| Sodium PCA | 0.50 |
| Hydrolyzed collagen | 2.00 |
| Xanthan gum | 1.40 |
| Sorbitol | 3.00 |
| Preservatives, dyes, perfume | q.s. |
| Green tea extract | 1.20 |
| Water | ad 100.00 |

EXAMPLE 15

Sunscreen emulsion

| | % by weight |
|---|---|
| Cyclomethicone | 2.00 |
| Cetyldimethicone copolyol | 0.20 |
| PEG 22 dodecyl copolymer | 3.00 |
| Paraffin oil (GP 9) | 2.00 |
| Caprylic/capric triglyceride | 5.80 |
| Octyl methoxycinnamate | 5.80 |
| Butylmethoxydibenzoylmethane | 4.00 |
| α-Glucosylrutin | 0.25 |
| Green tea extract | 0.50 |
| α-Tocopheryl acetate | 0.50 |
| $ZnSO_4$ | 0.70 |
| $Na_4EDTA$ | 0.30 |
| Preservatives, dyes, perfume | q.s. |
| Water | ad 100.00 |

EXAMPLE 16

Sunscreen emulsion

| | % by weight |
|---|---|
| Cyclomethicone | 2.00 |
| Cetylstearyl alcohol + PEG 40 hydrogenated castor oil + sodium cetylstearyl sulfate | 2.50 |
| Glyceryl lanolate | 1.00 |
| Caprylic/capric triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |

-continued

Sunscreen emulsion

| | % by weight |
|---|---|
| Hydroxypropylmethylcellulose | 0.30 |
| Octyl methoxycinnamate | 5.00 |
| Butylmethoxydibenzoylmethane | 0.50 |
| α-Glucosylrutin | 0.10 |
| Green tea extract | 0.20 |
| α-Tocopheryl acetate | 1.00 |
| Na₃HEDTA | 1.50 |
| Preservatives, dyes, perfume | q.s. |
| Mg ascorbyl phosphate | 0.50 |
| Water | ad 100.00 |

EXAMPLE 17

Sunscreen emulsion

| | % by weight |
|---|---|
| Cyclomethicone | 2.00 |
| Cetylstearyl alcohol + PEG 40 hydrogenated castor oil + sodium cetylstearyl sulfate | 2.50 |
| Glyceryl lanolate | 1.00 |
| Caprylic/capric triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.75 |
| α-Glucosylrutin | 0.50 |
| Na₃HEDTA | 1.50 |
| Preservatives, dyes, perfume | q.s. |
| Green tea extract | 3.00 |
| Water | ad 100.00 |

EXAMPLE 18

Spray formulation

| | % by weight |
|---|---|
| Green tea extract | 0.30 |
| Dihydrorobinetin | 0.80 |
| Ethanol | 28.20 |
| Preservatives, dyes, perfume | q.s. |
| Propane/butane 25/75 | ad 100.00 |

What is claimed is:

1. A method for stimulating melanogenesis in human skin, comprising applying to the skin a cosmetic or dermatalogical preparation containing an effective amount of one or more chosen from the group consisting of catechins, gallic esters of catechins, and aqueous or organic extracts from plants or parts of plants which have a content of catechins or gallic esters of catechins, the preparation being free of dihydroxyacetone.

2. The method as claimed in claim 1, wherein the catechins are chosen from the group consisting of (−)-catechin, (+)-catechin, (−)-catechin gallate, (−)-gallocatechin gallate, (+)-epicatechin, (−)-epicatechin, (−)-epicatechin gallate, (−)-epigallocatechin, and (−)-epigallocatechin gallate.

3. The method as claimed in claim 1, wherein the preparation comprises plant extracts having a content of catechins.

4. The method as claimed in claim 3, wherein the plant extract comprises extract from leaves of the Theaceae family.

5. The method as claimed in claim 4, wherein the plant extract comprises extract from green tea leaves.

6. A method for intensifying natural skin tanning or for stimulating melanogenesis in human skin, comprising applying to the skin a cosmetic or dermatological preparation containing an effective amount of a plant extract from leaves of the Theaceae family, the preparation being free of dihydroxyacetone.

7. The method as claimed in claim 6, wherein the plant extract comprises extract from green tea leaves.

* * * * *